US012806125B2

(12) United States Patent
Luo

(10) Patent No.: US 12,806,125 B2
(45) Date of Patent: Nov. 24, 2026

(54) COSMETIC

(71) Applicant: Shiseido Company, Ltd., Tokyo (JP)

(72) Inventor: Yuan Luo, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 858 days.

(21) Appl. No.: 18/030,386

(22) PCT Filed: Nov. 9, 2021

(86) PCT No.: PCT/JP2021/041079

§ 371 (c)(1),
(2) Date: Apr. 5, 2023

(87) PCT Pub. No.: WO2022/102592

PCT Pub. Date: May 19, 2022

(65) Prior Publication Data

US 2023/0372217 A1 Nov. 23, 2023

(30) Foreign Application Priority Data

Nov. 11, 2020 (JP) ................................ 2020-188038

(51) Int. Cl.

*A61K 8/44* (2006.01)
*A61K 8/02* (2006.01)
*A61Q 1/12* (2006.01)

(52) U.S. Cl.

CPC ................ *A61K 8/44* (2013.01); *A61K 8/022* (2013.01); *A61Q 1/12* (2013.01); *A61K 2800/34* (2013.01); *A61K 2800/43* (2013.01); *A61K 2800/612* (2013.01)

(58) Field of Classification Search

CPC ...... A61K 8/44; A61K 8/022; A61K 2800/34; A61K 2800/43; A61K 2800/612; A61K 8/0241; A61K 8/064; A61K 8/29; A61K 8/37; A61K 8/39; A61K 8/19; A61Q 1/12; A61Q 17/04; A61Q 1/02

See application file for complete search history.

(56) References Cited

U.S. PATENT DOCUMENTS

2014/0079656 A1* 3/2014 Clavel ...................... A61K 8/31
514/784

FOREIGN PATENT DOCUMENTS

| | | | | |
|---|---|---|---|---|
| JP | 2012121835 | A | * | 6/2012 |
| JP | 2013-121940 | A | | 6/2013 |
| JP | 2016222587 | A | * | 12/2016 |
| WO | WO-2010/061242 | A1 | | 6/2010 |

OTHER PUBLICATIONS

Kazuhiro; JP2016222587A; machine translation provided. (Year: 2016).*

Hirofumi; JP2012121835A—machine translation provided). (Year: 2012).*

JP2016222587A - machine translation provided. Kazuhiro "Water-In-Oil Emulsion Cosmetic" 2016. (Year: 2016).*

Daito Kasei "Product", 2018. (Year: 2018).*

Daito Kasei Europe "Ecocert" 2019. (Year: 2019).*

JP2012121835A—machine translation provided. Hirofumi "Lipophilically Surface Treated Powder Having Excellent Smooth Feeling and Detergency" 2012 (Year: 2012).*

Daito Kasei Europe Sas, Asl Treatment, Apr. 30, 2017, 2 pages, https://www.daitokasei.com/upload/product/file/file_en00000394.pdf.

Kobo Products Inc., ASI Yellow LL-100P, Jun. 30, 2018, 1 page, https://www.koboproductsinc.com/Specs/ASI-YELLOW-LL-100P_Specs.pdf.

* cited by examiner

*Primary Examiner* — Ali Soroush
*Assistant Examiner* — Rajan Pragani
(74) *Attorney, Agent, or Firm* — Foley & Lardner LLP

(57) ABSTRACT

The present invention addresses the problem of providing a silicone-free cosmetic containing no silicone compounds, not only in a surface treatment agent for a powder, but also in the cosmetic itself, wherein the cosmetic has excellent powder dispersibility, has a stable and clear appearance, and also has a good texture in use. The present invention relates to a cosmetic containing (A) a powder that is surface-treated with a surface treatment agent including at least two types of treatment agents, one of the at least two types of treatment agents being an N-acyl amino acid or a salt thereof; and (B) at least one type of surfactant selected from among polyglycerol esters of fatty acids; wherein the cosmetic does not contain a silicone compound.

6 Claims, No Drawings

COSMETIC

CROSS-REFERENCE TO RELATED APPLICATIONS

This application is the U.S. National Stage of PCT/JP2021/041079, filed Nov. 9, 2021, which claims priority to JP 2020-188038, filed Nov. 11, 2020.

TECHNICAL FIELD

The present invention relates to a cosmetic not containing a silicone compound. More specifically, the present invention relates to a cosmetic, particularly a makeup cosmetic, that does not contain a silicone compound, and that also has excellent stability and a good texture.

BACKGROUND ART

Silicone compounds such as silicone oils are used not only in hair cosmetics such as shampoos, but are also commonly used in cosmetics applied to the skin, such as foundations. Silicone compounds have the characteristics of high water repellence, a light texture in use without stickiness, and good spreadability on the hair and skin. Silicone compounds have, in the cosmetics in which they are blended, the effects of improving the water resistance, the texture in use, and the dispersibility of other blended components. Furthermore, silicone compounds are widely used also as surface treatment agents for powder components.

While silicone compounds have the advantages mentioned above, they also have problems such as making cosmetics difficult to remove with water due to their high water repellence, such that the cleansing required for washing stresses the skin. Furthermore, since silicone compounds are normally not biodegradable, there are concerns that they may accumulate in the environment for long periods of time, so there is a risk of contaminating the environment and disrupting ecosystems. Therefore, in recent years, there has been interest in cosmetics, called “silicone-free” or “non-silicone”, in which silicone compounds are not blended.

However, when the silicone compounds that contributed to increased dispersibility of other blended components such as powders in conventional cosmetics are removed, problems occur, such as the stability of the cosmetics becoming difficult to maintain. Additionally, regarding surface treatment agents for powders also, it has been proposed to improve the washability by using N-acyl amino acids rather than silicone compounds. Patent Document 1 describes that a water-in-oil emulsion cosmetic in which a combination of a specific surfactant and a powder surface-treated with an N-acyl amino acid or a salt thereof is blended has excellent makeup durability and washability.

However, although the cosmetic described in Patent Document 1 does not contain a silicone compound as a surface treatment agent, it contains a silicone oil as the medium of the cosmetic, and thus does not constitute a silicone-free cosmetic. If the silicone oil is removed from the cosmetic described in Patent Document 1 to make a silicone-free cosmetic, then the cosmetic has a tendency for the powder to re-aggregate during storage. Therefore, excellent powder dispersibility, a stable and clear appearance, and a good texture in use were not able to be obtained.

RELATED ART

Patent Documents

Patent Document 1: JP 6574613 B

SUMMARY OF THE INVENTION

Problem to be Solved by the Invention

The present invention addresses the problem of providing a silicone-free cosmetic containing no silicone compounds, not only in a surface treatment agent for a powder, but also in the cosmetic itself, wherein the cosmetic has excellent powder dispersibility such that the powder does not re-aggregate over time, has a stable and clear appearance, and also has a good texture in use.

Means for Solving the Problem

The present inventors performed diligent research towards solving the aforementioned problem, as a result of which they discovered that, by combining a surfactant having a specific structure with a powder (particularly a pigment) treated with a specific surface treatment agent, a stable cosmetic having excellent powder dispersibility, color development (color developing) property of pigment, and texture in use (smoothness) of the cosmetic can be obtained even without blending a silicone compound, thereby completing the present invention.

That is, the present invention provides a cosmetic containing.

(A) a powder that is surface-treated with a surface treatment agent including at least two types of treatment agents, one of the at least two types of treatment agents being an N-acyl amino acid or a salt thereof; and (B) at least one type of surfactant selected from among polyglycerol esters of fatty acids; wherein the cosmetic does not contain a silicone compound.

Effects of the Invention

The cosmetic of the present invention has good dispersibility of blended powders and is stable, even without blending a silicone compound. Additionally, the cosmetic of the present invention has excellent color development property of powder (pigment) and provides a smooth texture, even without blending an organic polymeric spherical powder.

MODES FOR CARRYING OUT THE INVENTION (A) Powder

The powder (also referred to as “component A”) blended in the cosmetic of the present invention is not particularly limited and can be selected, as appropriate, from among powder components that are blended in cosmetics, as long as the surface thereof has been treated with a surface treatment agent as described below. The powder (A) in the present invention is preferably selected from among white pigments including titanium oxide and zinc oxide, coloring pigments such as red iron oxide (Bengal red), yellow iron oxide and black iron oxide, extender pigments such as talc, mica, sericite, synthetic phlogopite and barium sulfate, and ultraviolet scattering agents such as fine-particle titanium oxide and fine-particle zinc oxide.

The powder (A) in the cosmetic of the present invention is a powder that is surface-treated with a surface treatment agent containing at least two types of treatment agents, one of the at least two types of treatment agents being N-acyl amino acid or a salt thereof. By using such a powder that is surface-treated with a specific treatment agent, a cosmetic having excellent powder dispersibility, color development properties and texture is obtained.

The "N-acyl amino acid or a salt thereof" contained in the surface treatment agent of the present invention is a compound having an acyl group, preferably a saturated fatty acid having 12 to 20 carbon atoms, condensed onto an amino group of an amino acid, or a salt of such a compound. The "amino acid" is preferably glutamic acid or aspartic acid. The "N-acyl group" may be a stearoyl group, a lauroyl group or the like. The "salt" may be selected from among alkali metal salts such as sodium and potassium, alkaline earth metal salts or the like, among which a sodium salt is preferable. Specific examples include disodium N-stearoyl glutamate, sodium N-lauroyl glutamate and sodium lauroyl aspartate.

The surface treatment agent in the present invention includes at least one other treatment agent in addition to the aforementioned "N-acyl amino acid or a salt thereof". The "other treatment agent" is preferably selected from among an "amino acid", an "ester" and a "metal complex of an ester". The "amino acid" is not particularly limited, but is preferably selected from among aspartic acid, glutamic acid and lysine, among which lysine is particularly preferable. The "ester" is a compound obtained by bonding, by an ester bond, a monovalent or divalent fatty acid having 8 to 12 carbon atoms with a saturated aliphatic alcohol having 12 to 20 carbon atoms. The alkyl chain in the fatty acid or the aliphatic alcohol may be straight or branched. In particular, isostearyl sebacate is preferably used. The "metal complex of an ester" is a compound obtained by coordinate-bonding an ester to a metal atom. For example, isopropyl titanium triisostearate can be named as a preferable example.

The powder (A) used in the present invention is preferably a powder surface-treated with a surface treatment agent (NHS treatment agent) containing disodium N-stearoyl glutamate and isostearyl sebacate, a surface treatment agent (ASL treatment agent) containing sodium N-lauroyl glutamate and lysine, or a surface treatment agent (ASI treatment agent) containing sodium lauroyl aspartate and isopropyl titanium triisostearate. Among the above, a powder surface-treated with an NHS treatment agent or an ASL treatment agent is particularly preferable.

A commercially available product may be used as the powder (A). Preferable commercially available products include, for example, NHS treatment powders such as NHS-titanium CR-50, NHS-Red R516PS, NHS-Yellow LL-100P, NHS-Black BL-100P, NHS-Mica M-102 and NHS-talc JA-46R (all manufactured by Miyoshi Kasei Industry Co., Ltd.); ASL treatment powders such as ASL-1 TiO2 CR-50, ASL-Red R516P, ASL-Yellow LL-100P and ASL-Black BL-100P; and ASI treatment powders such as ASI TiO2 CR-50, ASI-Red R516P, ASI-Yellow LL-100P, ASI-Black BL-100P and ASI-Talc JA46R (all manufactured by Daito Kasei Kogyo Co., Ltd.).

The cosmetic of the present invention may be obtained by blending one or a combination of two or more of the aforementioned powders (A) treated with the aforementioned surface treatment agent, the total blended amount thereof being 0.5% to 40% by mass, preferably 5% to 30% by mass, relative to the overall amount of the cosmetic.

(B) Surfactant

The surfactant (also referred to as "component (B)") used in the cosmetic of the present invention is at least one type selected from among polyglycerol esters of fatty acids. The fatty acid constituting the polyglycerol ester of a fatty acid is preferably selected from among monovalent (monohydroxy) fatty acids having 12 to 22 carbon atoms. For example, a saturated monovalent fatty acid such as isostearic acid or an unsaturated monovalent fatty acid such as ricinoleic acid is preferable, among which a ricinoleic acid polymer is particularly preferable.

As the polyglycerol ester of a fatty acid, one having 3 to 8 polyglycerin repeat units is preferable. In the present invention, it is particularly preferable to use polyglyceryl-6 polyricinoleate as the surfactant (B).

The blended amount of the (B) surfactant in the cosmetic of the present invention can be decided, as appropriate, in accordance with the specific surface area, the particle size and the blended amount of the powder of component (A) above, but should normally be 0.1% to 15% by mass, preferably 0.5% to 10% by mass, relative to the overall amount of the cosmetic. Within the ranges described above, it is possible to obtain a cosmetic having excellent powder dispersibility such that the powder does not re-aggregate over time, having a stable and clear appearance, and also having a good texture in use.

The cosmetic of the present invention is a "silicone-free" cosmetic that does not contain silicone compounds.

The "silicone compounds" in the present specification refer to compounds (e.g., silicones and siloxanes) having siloxane structures (—Si—O—Si—) in their molecules, and silanes (monosilanes, oligosilanes, polysilanes and silane derivatives, e.g., alkylsilane, alkoxysilane, etc.). These include silicone oils, silicone elastomers and silicone-based surfactants, as well as powders surface-treated with silicone compounds. Silicon oxide (silica) is not included among the "silicone compounds" in the present invention.

The cosmetic of the present invention, by combining the above-mentioned powder (A) treated with a specific surface treatment agent and the above-mentioned specific surfactant (B), has excellent powder dispersibility, has a stable and clear appearance, and also has a good texture in use, even as a silicone-free cosmetic.

The cosmetic of the present invention can be prepared as a water-in-oil emulsion cosmetic, an oil-in-water emulsion cosmetic or an oil-based liquid cosmetic. However, it is preferably a water-in-oil emulsion cosmetic because, in that case, the advantageous effects of the present invention can more easily be obtained.

The oils constituting the oil phase should be oils other than silicone oils, including, for example, hydrocarbon oils, ester oils, higher alcohols having 12 to 22 carbon atoms, fatty acids having 12 to 22 carbon atoms and the like.

Hydrocarbon oils include, for example, liquid paraffin, liquid isoparaffins such as hydrogenated polyisobutene, heavy liquid isoparaffin, liquid ozokerite, squalane, pristane, squalene, volatile hydrocarbon oils (for example, isododecane, isohexadecane, undecane, tridecane, etc.) and the like.

Ester oils include, for example, isononyl isononanoate, isotridecyl isononanoate, octyldecyl myristate, isopropyl myristate, isocetyl myristate, alkyl benzoates such as alkyl (C12-C15) benzoate, monoester oils such as isopropyl palmitate, ethylhexyl palmitate and 2-hexyldecyl palmitate, diester oils such as 2-ethylhexyl sebacate, diisopropyl sebacate, diethylene glycol dicaprate, neopentyl glycol dicaprate, neopentyl glycol di-2-ethylhexanoate and diisostearyl malate, triester oils such as glyceryl tri-2-ethylhexanoate, glyceryl tri(caprylate/caprate) and the like.

Higher alcohols having 12 to 22 carbon atoms include, for example, oleyl alcohol, 2-decyltetradecinol, dodecanol, isostearyl alcohol, octyl dodecanol and the like. Fatty acids having 12 to 22 carbon atoms include, for example, oleic acid, isostearic acid, linolic acid, linoleic acid and the like.

The cosmetic of the present invention may contain, in addition to the above, other optional components that are normally used in cosmetics or the like, blended within a range not inhibiting the effects of the present invention. The other optional components include, for example, powders other than component (A) above, surfactants other than component (B) above, polymer compounds, ultraviolet absorbers, antioxidants, fragrances, colorants, preservatives, microbicides, various medicinal agents, humectants and the like.

The powders other than component (A) are not particularly limited, but should preferably not contain microplastic beads (MPBs) from the aspect of protecting the environment in recent years. "Microplastic beads (MPBs)" are understood, in the narrow sense, to be "synthetic non-water-soluble solid plastic particles having a size smaller than 5 mm, intentionally blended into personal care products for the purpose of washing and removing dead skin". However, in the present specification, "MPBs" include, in addition to the aforementioned MPBs in the narrow sense, organic polymer spherical particles and powders treated with polymerized surface treatment agents that have conventionally been blended for the purpose of improving the texture of cosmetics. The cosmetic of the present invention achieves a smooth texture in use by combining the aforementioned components (A) and (B).

The cosmetic of the present invention can be produced in accordance with a normal method, and can be in a form such as liquid, emulsion, paste, cream, gel or solid.

The cosmetic of the present invention may be provided as a makeup cosmetic such as a makeup base, a foundation, a concealer, a blush, an eyeshadow, a mascara, an eyeliner, an eyebrow pencil, an overcoat, a lipstick or the like; or as a skin-care cosmetic such as a sunscreen, among which it is well-suited to being a makeup cosmetic, particularly a liquid foundation.

EXAMPLES

The present invention will be explained in further detail below by describing examples below. However, the present invention is not limited by these examples. The blended amounts are indicated in percentage by mass where not described otherwise.

Water-in-oil emulsion cosmetics were prepared by using conventional methods in accordance with Formulation 1 or Formulation 2 given in Table 1 below.

TABLE 1

| | Formulation 1 | Formulation 2 |
|---|---|---|
| Volatile hydrocarbon oil | 25 | 20 |
| Isopropy myristate | — | 3 |
| Ethylhexyl methoxycinnamate | — | 2 |
| Isostearic acid | 1 | — |
| Diisostearyldimonium hectorite | 1 | — |
| Polyglyceryl-2-diisostearate | 4 | 4 |
| Polyglyceryl-6 polyricinoleate | 0.7 | 0.7 |
| Tocopherol | 0.02 | 0.02 |
| White pigment (*) | 10 | 10 |
| Yellow pigment (*) | 1 | 1 |
| Red pigment (*) | 0.25 | 0.25 |
| Black pigment (*) | 0.1 | 0.1 |
| Fine-particle titanium oxide | 2 | 2 |
| Glycerin | 1 | 1 |
| 1,3-BG | 3 | 3 |
| Sodium chloride | 1 | 1 |
| Phenoxyethanol | 0.5 | 0.5 |
| Water | balance | balance |
| Total | 100 | 100 |

Pigments treated with the surface treatment agents indicated in Table 2 below were used as the "pigment" (*) in Table 1, and each cosmetic was evaluated regarding powder dispersibility, color development properties, and texture in use (smoothness). The evaluation results are also shown in Table 2.

A: Good

B: Normal

C: Somewhat poor

D: Poor

TABLE 2

| | | Ex. 1 | Ex. 2 | Ex. 3 | Comp. Ex. 1 | Comp. Ex. 2 |
|---|---|---|---|---|---|---|
| Surface treatment agent | | Disodium N-stearoyl glutamate + isostearyl sebacate (*1) | Sodium N-lauroyl glutamate + lysine (*2) | Sodium lauroyl aspartate + isopropyl titanium triisostearate (*3) | Lauroyl lysine (*4) | Disodium stearoyl glutamate (*5) |
| Formulation | | 1 or 2 | 1 or 2 | 2 | 1 | 1 |
| Evaluati | Dispersibility | A | A | A | C | D |
| | Color development | A | A | B | C | A |
| | Texture | A | A | A | C | A |

(*1): NHS-treated pigment (manufactured by Miyoshi Kasei Industry Co., Ltd.)

(*2): ASL-treated pigment (manufactured by Daito Kasei Kogyo Co., Ltd.)

(*3): ASI-treated pigment (manufactured by Daito Kasei Kogyo Co., Ltd.)

(*4): LL-treated pigment (manufactured by Daito Kasei Kogyo Co., Ltd.)

(*5): NAI-treated pigment (manufactured by Miyoshi Kasei Industry Co., Ltd.)

As indicated in Table 2, the cosmetics containing pigments treated with a surface treatment agent (NHS treatment) containing disodium N-stearoyl glutamate and isostearyl sebacate, a surface treatment agent (ASL treatment) containing sodium N-lauroyl glutamate and lysine, or a surface treatment agent (ASI treatment) containing sodium lauroyl aspartate and isopropyl titanium triisostearate, i.e., a surface treatment agent containing two or more treatment agents including an N-acyl amino acid or a salt thereof, performed excellently in all properties that were evaluated. Among the above, the cosmetics containing pigments surface-treated with a surface treatment agent (NHS treatment) containing disodium N-stearoyl glutamate and isostearyl sebacate or a surface treatment agent (ASL treatment) containing sodium N-lauroyl glutamate and lysine had particularly excellent properties.

Next, oil-based liquid cosmetics were prepared in accordance with a conventional method using the formulations indicated in Table 3 below, and the powder dispersibility of each cosmetic was evaluated. The evaluation method and the ranking of properties were performed similarly to those in Table 2. The evaluation results are also shown in Table 3.

(liquid form) cosmetic, by combining a specific surfactant (B) with a powder (A) treated with a specific surface treatment (Examples 4 and 5). In contrast therewith, the dispersibility decreased in examples using surfactants other than the polyglycerol esters of fatty acids in the present invention and examples in which surfactants were not added (Comparative Examples 3 to 8). Additionally, the dispersibility was poor, regardless of the type of surfactant, in examples using silicone compounds as oils (Comparative Examples 9 to 13).

Next, cosmetics were prepared with the formulations indicated in Table 4 below, and the cosmetics were evaluated for powder dispersibility, texture (smoothness) when applied, and stability of the emulsion state over time (four weeks). The evaluation method and the ranking of the powder dispersibility were performed similarly to those in Table 2 and Table 3. The texture (smoothness) during application was evaluated by five expert panelists, and the texture (smoothness) was represented by the number of "+" signs. The greater the number of "+" signs, the higher the evaluation was (though even with just a single "+" sign, there are no problems in terms of practical use). The stability of the emulsion state was evaluated by visual observation of the presence or absence of changes in the appearance, and by measurement of the presence or absence of viscosity changes using a Brookfield viscometer (BL type).

TABLE 3

| | Ex. | | Comp. Ex. | | | | | | | | | | |
|---|---|---|---|---|---|---|---|---|---|---|---|---|---|
| Component | 4 | 5 | 3 | 4 | 5 | 6 | 7 | 8 | 9 | 10 | 11 | 12 | 13 |
| Isododecane | 80 | | 80 | 80 | 80 | 80 | 83 | — | — | — | — | — | — |
| Isopropyl myristate | — | 80 | — | — | — | — | — | 83 | — | — | — | — | — |
| Dimethylpolysiloxane | — | — | — | — | — | — | — | — | 83 | 80 | 80 | 80 | 80 |
| Sodium N-lauroyl glutamate and lysine (ASL)-treated red iron oxide | 16 | 16 | 16 | 16 | 16 | 16 | 17 | 17 | 17 | 16 | 16 | 16 | 16 |
| Polyglyceryl-6 polyricinoleate | 4 | 4 | — | — | — | — | — | — | — | 4 | — | — | — |
| Polyglyceryl-2 diisostearate | — | — | 4 | — | — | — | — | — | — | — | 4 | — | — |
| Sorbitan sesquiisostearate | — | — | — | 4 | — | — | — | — | — | — | — | 4 | — |
| Pentaerythrity1 tetraethylhexanoate | — | — | — | — | 4 | — | — | — | — | — | — | — | — |
| PEG-9 polydimethyl siloxymethyl dimethicone | — | — | — | — | — | 4 | — | — | — | — | — | — | — |
| PEG-10 dimethicone | — | — | — | — | — | — | — | — | — | — | — | — | 4 |
| Total | 100 | 100 | 100 | 100 | 100 | 100 | 100 | 100 | 100 | 100 | 100 | 100 | 100 |
| Dispersibility | A | A | B | B | C | C | C | B | D | D | D | D | D |

As indicated in Table 3, good powder dispersibility was obtained, whether using either a volatile hydrocarbon oil or a non-volatile ester oil as the oil in the oil-based liquid ○: Changes in appearance and viscosity were not observed.

x: Changes in appearance or viscosity were observed.

TABLE 4

| Components | Ex. 6 | Ex. 7 | Ex. 8 | Ex. 9 | Comp. Ex. 14 | Comp. Ex. 15 |
|---|---|---|---|---|---|---|
| Volatile hydrocarbon oil | 20 | 20 | 20 | 20 | 20 | — |
| Dimethylpolysiloxane | — | — | — | — | — | 20 |
| Isopropyl myristate | 5 | 5 | 5 | 5 | 5 | 5 |
| Diisostearyldimonium hectorite | 1 | 1 | 1 | 1 | 1 | 1 |
| Tocopherol | 0.02 | 0.02 | 0.02 | 0.02 | 0.02 | 0.02 |
| Polyglyceryl-2 diisostearate | 5 | 3 | 2 | 0 | 5 | 3 |
| Polyglyceryl-6 polyricinoleate | 1 | 3 | 4 | 5 | 0 | 3 |
| White pigment (ASL-treated) | 11.5 | 11.5 | 11.5 | 11.5 | 11.5 | 11.5 |
| Yellow pigment (ASL-treated) | 2.8 | 2.8 | 2.8 | 2.8 | 2.8 | 2.8 |
| Red pigment (ASL-treated) | 0.77 | 0.77 | 0.77 | 0.77 | 0.77 | 0.77 |
| Black pigment (ASL-treated) | 0.43 | 0.43 | 0.43 | 0.43 | 0.43 | 0.43 |
| Mica | 2 | 2 | 2 | 2 | 2 | 2 |
| Glycerin | 1 | 1 | 1 | 1 | 1 | 1 |
| 1,3-BG | 7 | 7 | 7 | 7 | 7 | 7 |
| Sodium chloride | 1 | 1 | 1 | 1 | 1 | 1 |
| Phenoxyethanol | 0.5 | 0.5 | 0.5 | 0.5 | 0.5 | 0.5 |
| Water | balance | balance | balance | balance | balance | balance |
| Total | 100 | 100 | 100 | 100 | 100 | 100 |
| Powder dispersibility | A | A | A | A | B | D |
| Texture (smoothness) when applied | + | ++ | +++ | ++++ | + | ++ |
| Stability of emulsion state | ○ | ○ | ○ | ○ | x | x |

As indicated in Table 4, Comparative Example 14, in which only polyglyceryl-2 diisostearate was used as the surfactant (B), was able to be used stably without problems for a number of days immediately after formulation. However, the emulsion broke down after four weeks passed. Additionally, in Comparative Example 15, in which a silicone oil was used, the powder dispersibility became lower and the emulsion stability became inadequate immediately after preparation, so a cosmetic with a clear appearance was not able to be obtained. In contrast therewith, Examples 6 to 9, in which polyglyeryl-6 polyricinoleate was used, maintained excellent stability even after four weeks

The invention claimed is:

1. A cosmetic containing:

(A) a powder that is surface-treated with a surface treatment agent including at least two types of treatment agents, one of the at least two types of treatment agents being an N-acyl amino acid or a salt thereof; and (B) at least one type of surfactant selected from among polyglycerol esters of fatty acids;

wherein the cosmetic does not contain a silicone compound, and wherein (A) the powder is a powder surface-treated with a surface treatment agent containing disodium N-stearoyl glutamate and isostearyl sebacate, a powder surface-treated with a surface treatment agent containing sodium N-lauroyl glutamate and lysine, or a powder surface-treated with a surface treatment agent containing sodium lauroyl aspartate and isopropyl titanium triisostearate.

2. The cosmetic according to claim 1, wherein the powder (A) is a powder surface-treated with a surface treatment agent containing disodium N-stearoyl glutamate and isostearyl sebacate, or a powder surface-treated with a surface treatment agent containing sodium N-lauroyl glutamate and lysine.

3. The cosmetic according to claim 1, wherein the surfactant (B) is a polyglycerol ester of a monohydroxy fatty acid having 12 to 22 carbon atoms.

4. The cosmetic according to claim 1, wherein the surfactant (B) is polyglyceryl-6 polyricinoleate.

5. The cosmetic according to claim 1, which is a water-in-oil emulsion cosmetic.

6. The cosmetic according to claim 1, which is an oil-based liquid cosmetic.

* * * * *